(12) United States Patent
Guan et al.

(10) Patent No.: US 10,395,764 B2
(45) Date of Patent: Aug. 27, 2019

(54) METHOD AND APPARATUS FOR RECOGNITION OF PATIENT ACTIVITY

(71) Applicant: AIC Innovations Group, Inc., New York, NY (US)

(72) Inventors: Lei Guan, Jersey City, NJ (US); Dehua Lai, Lawrenceville, NJ (US)

(73) Assignee: AIC Innovations Group, Inc., New York, NY (US)

( * ) Notice: Subject to any disclaimer, the term of this patent is extended or adjusted under 35 U.S.C. 154(b) by 577 days.

(21) Appl. No.: 14/590,026

(22) Filed: Jan. 6, 2015

(65) Prior Publication Data
US 2016/0196503 A1 Jul. 7, 2016

(51) Int. Cl.
*G06N 7/02* (2006.01)
*G06N 7/04* (2006.01)
*G06N 7/06* (2006.01)
*G06N 7/08* (2006.01)
*G16H 10/60* (2018.01)
*G16H 20/10* (2018.01)
*G06K 9/00* (2006.01)
*G06K 9/62* (2006.01)
*G06N 3/04* (2006.01)
*G06N 3/08* (2006.01)
*A61B 19/00* (2006.01)

(52) U.S. Cl.
CPC ......... *G16H 10/60* (2018.01); *G06K 9/00228* (2013.01); *G06K 9/00375* (2013.01); *G06K 9/62* (2013.01); *G06N 3/0454* (2013.01); *G06N 3/08* (2013.01); *G16H 20/10* (2018.01); *A61B 19/44* (2013.01)

(58) Field of Classification Search
CPC combination set(s) only.
See application file for complete search history.

(56) References Cited

U.S. PATENT DOCUMENTS

| 5,251,626 A | 10/1993 | Nickolls et al. |
| 9,317,916 B1 * | 4/2016 | Hanina ................. G06T 7/0012 |
| 2003/0147558 A1 * | 8/2003 | Loui ................. G06K 9/00624 382/225 |

(Continued)

OTHER PUBLICATIONS

Saxe et al. *Learning hierarchical category structure in deep neural networks*, Proc. of the 11-20 Cognitive Science Society, (2013), Retrieved on [Feb. 23, 2016], retrieved from the internet. <URL: http://waldron.stanford.edu/~jlm/papers/SaxeMcCGanguli_13CogSciProc.pdf> (7 pages).

(Continued)

*Primary Examiner* — Kakali Chaki
*Assistant Examiner* — Ababacar Seck
(74) *Attorney, Agent, or Firm* — Fish & Richardson P.C.

(57) ABSTRACT

A system and method for training a system for monitoring administration of medication. The method includes the steps of a method for training a medication administration monitoring apparatus, comprising the steps of defining one or more predetermined medications and then acquiring information from one or more data sources of a user administering medication. A first network is trained to recognize a first step of a medication administration sequence, and then a second network is trained to recognize a second step of a medication administration sequence based upon the training of the first network.

10 Claims, 5 Drawing Sheets

(56) References Cited

U.S. PATENT DOCUMENTS

| | | | |
|---|---|---|---|
| 2009/0048871 A1 | 2/2009 | Skomra | |
| 2011/0275051 A1* | 11/2011 | Hanina | G06F 19/3418 434/365 |
| 2012/0219176 A1* | 8/2012 | Guan | G06K 9/00355 382/103 |
| 2012/0316897 A1* | 12/2012 | Hanina | G06F 19/3456 705/3 |
| 2013/0044196 A1 | 2/2013 | Guan et al. | |
| 2013/0169781 A1 | 7/2013 | Hanina et al. | |
| 2013/0279774 A1* | 10/2013 | Helgason | A61J 7/0084 382/128 |
| 2014/0184772 A1 | 7/2014 | Hanina et al. | |
| 2014/0214448 A1 | 7/2014 | Hanina et al. | |

OTHER PUBLICATIONS

International Search Report and Written Opinion, dated Mar. 4, 2016, for International Application No. PCT/US2015/067796 (10 pages).

Ngiam, Jiquan; Khosla, Aditya; Kim, Mingyu; Lee, Honglak; Ng, Andrew Y.; *Multimodal Deep Learning*; Proceedings of the 28$^{th}$ International Conference on Machine Learning, Bellevue, WA, USA; 2011.

EP Supplemental Search Report and Opinion for EP App No. 15877360.6, dated Jul. 27, 2018 (13 pages).

Wikipedia, *Classifier chains*, [online] May 7, 2018 (3 pages).

Zaamout and Zhang, *Improving Neuroal Networks Classification through Chaining*, Artificial Neural Networks and Machine Learning ICANN 2012, Springer Berlin Heidelberg, pp. 288-295 (Sep. 11, 2012).

\* cited by examiner

METHOD AND APPARATUS FOR RECOGNITION OF PATIENT ACTIVITY

FIELD

This invention relates generally to recognition of patient activity, and more particularly to a method and apparatus for the recognition of patients properly taking their medication for use with a medication monitoring system employing video, audio and other data captured, allowing for a diverse set of data to be employed in determining proper patient activity related to medication adherence.

BACKGROUND

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. As has been shown in regards to various public health medication administration situations, such as administration of tuberculosis medication by the WHO, Directly Observed Treatment (DOT) improves compliance of patients. *Global Tuberculosis Control: A Short Update to the* 2009 *Report*, World Health Organization, 2009. As is shown in this report, funding for implementing DOT programs is high. Thus, the ability to implement such a program with less of a financial burden would be desirable.

The total healthcare cost of drug-related morbidity, including poor adherence, is estimated at $290 billion per year in the US. Treatment of patients with poor adherence can require twice the resources from the healthcare system than treatment of more compliant individuals. Mortality and morbidity rates are much higher for patients who do not follow their prescribed drug therapy, especially for patients suffering from a chronic illness. Currently, 75% of healthcare spending in the US is directed towards treatment of chronic disease. These same chronically ill patients who are also non-adherent to their medication prescriptions are twice as likely to be hospitalized. Low levels of medication adherence also contribute to the high costs of clinical trials. In the US, patient recruitment is estimated at $6533 per individual and up to three times that amount to replace someone who has left. As a result, the number of clinical trials conducted abroad has been increasing. By 2012, an estimated 65% of FDA-regulated clinical trials will be conducted outside of the US, raising issues around regulation and supervision.

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series*, 2008 *Patient Adherence Update: New Approaches for Success*, October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. Similar failure to adhere to medication prescriptions plagues the population health management field. It is against this backdrop of poor adherence, and potential danger to patients, that the present invention operates.

Traditional monitoring methods have problems with reliability and cost, and may place a substantial burden on the patient. Pill counting and patient interviews are unreliable ways of measuring medication adherence, as is evidenced in the above studies, as they offer no information on the time of day medication is taken or whether the patient has skipped doses entirely. Self-reporting by individuals, even employing ePRO diaries, IVRS or web portal communications have also been shown to be untrustworthy as many patients fail to record accurate data. Technologically advanced solutions, such as digital pill container caps and smart packaging report only when the patient has opened the medication container and cannot confirm medication administration. Smart pills, while accurate, are expensive, require a modification to the manufacturing process, and are inconvenient for the patient. Even if patients are not intentionally deceptive, barriers to medication adherence such as the perceived impact of a medicine, knowledge about illness, forgetfulness, or lack of social support, are contributing factors to why 75% of Americans do not take their medicine as prescribed.

An extremely effective way to confirm medication adherence is through direct observation. The WHO's Directly Observed Treatment, short course (DOTs) program has radically improved overall compliance rates of TB patients. Indeed, such direct observation is typically employed in phase 1 clinical trials, where assurance of adherence is critical. Unfortunately, the labor-intensive nature of the program—hiring care workers to directly monitor patients—is expensive, and places a substantial burden on the patient. The inventors of the present invention provide an automated virtual direct observation solution, AiView® that may be applied to larger populations for a fraction of the cost of DOTs. AiView® leverages the increasing familiarity and access to webcam-enabled devices by incorporating a gesture and object recognition monitoring platform. Traditionally, participants attend introductions and follow ups for clinical trials, or in other disease management situations, in-person. Once the initial startup has been performed, however, patients are typically on their own to confirm that they are properly taking their medication. Infrequent check-ups, typically every few weeks or longer, have proven to be insufficient. A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or ingestion of the medication, or the relationship of adherence to the efficacy or safety of the drug over time. When requiring adherence to a predetermined protocol for a clinical trial, this is particularly relevant. Similarly, there is no mention of non-pill based medications. Furthermore, there is an assumption that a medication has been already trained to be recognized by the system, an assumption that may cause a problem given the number of different possible medications, including generic medications, that may be taken by an individual in accordance with a particular prescription.

Therefore, it would be desirable to provide an apparatus that overcomes the drawbacks of the prior art.

SUMMARY

In U.S. patent application Ser. No. 12/620,686, filed Nov. 18, 2009, titled Method and Apparatus for Verification of Medication Administration Adherence, abandoned; U.S. patent application Ser. No. 13/558,377, filed Jul. 26, 2012, titled Method and Apparatus or Verification of Medication Administration Adherence, now U.S. Pat. No. 8,781,856; U.S. patent application Ser. No. 14/295,485, filed Jun. 4, 2014, titled Method and Apparatus for Verification of Medication Administration Adherence, currently pending; U.S. patent application Ser. No. 12/646,383, filed Dec. 23, 2009, titled Method and Apparatus for Verification of Clinical Trial Adherence, abandoned; U.S. patent application Ser. No. 13/558,380, filed Jul. 26, 2012, titled Method and Apparatus for Verification of Clinical Trial Adherence, now U.S. Pat. No. 8,731,961; U.S. patent application Ser. No. 14/244,035, filed Apr. 3, 2014, titled Method and Apparatus for Verification of Medication Adherence, currently pending; U.S. patent application Ser. No. 12/646,603, filed Dec. 23, 2009, titled Method and Apparatus for Management of Clinical Trials, now U.S. Pat. No. 8,666,781; U.S. patent application Ser. No. 14/153,042, filed Jan. 12, 2014, titled Method and Apparatus for Managing Medication Adherence, currently pending; U.S. patent application Ser. No. 12/728,721, filed Mar. 22, 2010, titled Apparatus and Method for Collection of Protocol Adherence Data, currently pending; U.S. patent application Ser. No. 12/815,037, filed Jun. 14, 2010, titled Apparatus and Method for Recognition of Patient Activities when Obtaining Protocol Adherence Data, currently pending; U.S. patent application Ser. No. 13/189,518, filed Jul. 24, 2011, titled Method and Apparatus for Monitoring Medication Adherence, currently pending; U.S. patent application Ser. No. 13/235,387, filed Sep. 18, 2011, titled Apparatus and Method for Recognition of Patient Activities, currently pending; U.S. patent application Ser. No. 13/674,209, filed Nov. 12, 2012, titled Method and Apparatus for Identification, currently pending; and U.S. patent application Ser. No. 13/674,459, filed Nov. 12, 2012, titled Method and Apparatus for Recognition of Inhaler Actuation, currently pending; the contents of these applications being incorporated herein by reference, the inventors of the present invention have proposed a system, method and apparatus that allow for complete control and verification of adherence to a prescribed medication protocol or machine or apparatus use in a clinical trial or disease management setting, whether in a health care provider's care, or when self-administered in a homecare situation by a patient.

These applications present the only medication management system that may determine whether a user is actually following a protocol, including properly determining whether the user has ingested their medication, such as by placing the medication in their mouth or the like, in real time, provide additional assistance in real time to a user, starting with instructions, such as audio and/or video/visual instructions, and the like, and moving up to contact from a medication administrator if it is determined that the user would need or benefit from such assistance in any medical adherence situation, including clinical trial settings, home care settings, healthcare administration locations, such as nursing homes, clinics, hospitals and the like, and in clinical trial settings. Additional training may be provided in accordance with the real-time feedback so that the user can be further assisted in properly performing steps associated with proper medication adherence.

The inventive solution, in accordance with one or more embodiments of the present invention, recognizes the need to be able to apply the above described system to determine whether a user has taken their medication in a great number of scenarios where knowledge of the visual characteristics of the medication to be taken may not be known, or where the number of medications to be monitored by the system may be very large. In accordance with one or more embodiments of the present invention, a plurality of input data types are preferably employed to not only identify the medication, but to also determine whether a user has taken their medication. In particular, video and audio data may be employed to determine whether a user has taken their medication. Additionally, one or more of time on task data, past medication adherence data for the user or a population, usability data, intervention data and the like may be employed in one or more various combinations to determine whether a user has properly taken their medications. Additionally, the combination of these various data may be performed employing a fusion learning process, or one or more other supervised or unsupervised learning processes. In such a manner, the multiple data sources are employed to provide a best predictive model for classifying future input data and determining whether a user has properly performed one or more activities, and more particularly to determine whether a user has properly taken their medication.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which:

FIG. 5 is a flowchart diagram depicting a method for training a computer system using a further data source combination using a plurality of learning processes; and.

DETAILED DESCRIPTION

The invention will now be described making reference to the following drawings in which like reference numbers denote like structure or steps.

The method may be implemented on a general purpose computer, a purposefully built system, or any other computing system including one or more non-transitory computer readable storage medium. Various communication systems may be employed, such as wifi, cellular or other private network. The computing system may be a local device including processor, memory, camera and display. Alternatively, one or more of these elements may be located at a remote location, such as employing cloud storage and/or processing.

The system may be further applied to any type of visual recognition system, such as facial recognition or the like. The system may also be applied to voice or other sound recognition, thus allowing for a number of reference sounds to be trained, and other sounds to be indexed therefrom in the manner as described above. Other biometric identification systems may be included such as fingerprints, retinal scan, or the like.

Figure 1:
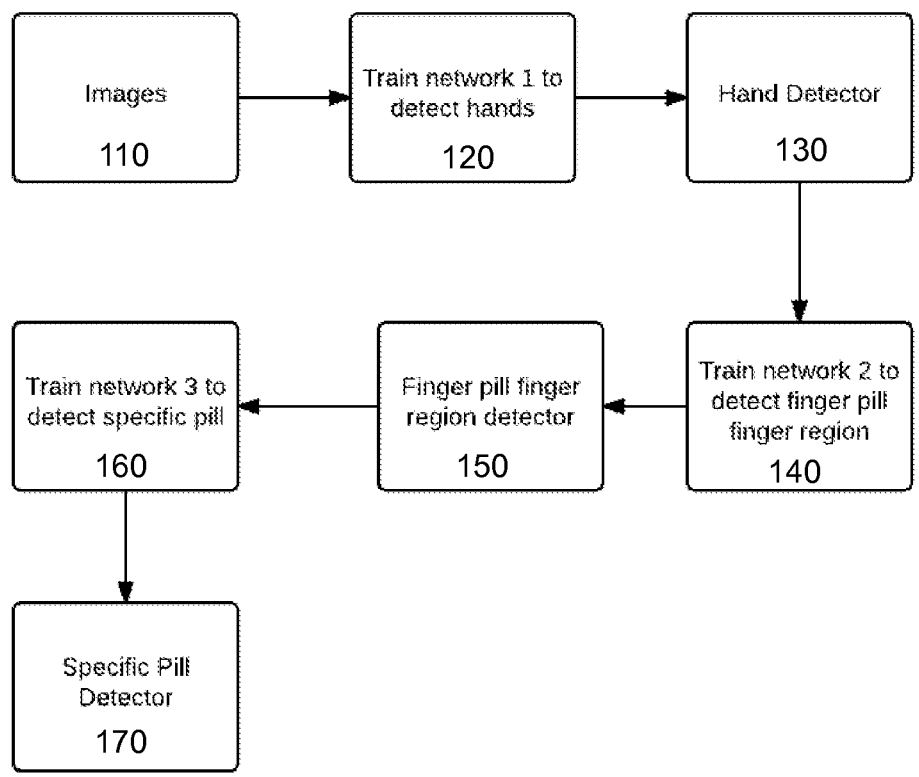
FIG. 1 is a flowchart diagram depicting a method for training a computer system in accordance with an embodiment of the invention.

Referring first to FIG. 1, a method for training a computer system for assisting in determining proper medication adherence, is provided. As is shown in FIG. 1, images are acquired at step 110. Preferably, in accordance with one or more embodiments of the present invention, such images are of a user administering a medication, such as a medication pill being held in the hand of the user. Such images may comprise individual still images, or may include one or more sets of sequential images, or one or more video sequences. Processing then preferably passes to step 120, where a first network is employed in accordance with one or more supervised or unsupervised learning processes, such as those known to one of ordinary skill in the art, in order to train the computer system to recognize the hand of the user. After such training has taken place, processing preferably passes to step 130 where the training data is employed in a hand detector element for detecting the hands of a future user when administering medication.

Processing then passes to step 140 where a second network is employed in accordance with one or more supervised or unsupervised learning processes, such as those known to one of ordinary skill in the art, in order to train the computer system to recognize a region including the finger-pill-finger region from the acquired one or more images. Such second network preferably builds on, or employs the first network employed in step 120. Thus, preferably, learning performed from the first network, or the output therefrom, is used as the input to the second network. In such a manner, the search space for the second network is bounded as the results from the first network are employed. Thus, this second network is preferably trained to determine a finger-pill-finger region from the determined hand regions identified by the first network. After such training has taken place, processing preferably passes to step 150 where the training data is employed in a finger-pill-finger detector element for detecting the finger-pill-finger region of a future user when administering medication.

Processing then passes to step 160 where a third network is employed in accordance with one or more supervised or unsupervised learning processes, such as those known to one of ordinary skill in the art, in order to train the computer system to recognize a particular medication pill from the acquired one or more images. Such third network preferably builds on, or employs the second network employed in step 140. Thus, preferably, learning performed from the second network, or the output therefrom, is used as the input to the third network. In such a manner, the search space for the third network is bounded as the results from the second network are employed. Thus, this third network is preferably trained to determine a pill region from the determined finger-pill-finger regions identified by the second network. After such training has taken place, processing preferably passes to step 170 where the training data is employed in a pill detector element for detecting the particular pill being administered by a future user when administering medication.

While the method has been described in a particular order, it is possible that any order of training and deployment may be employed. Further, it is possible to use any sub-group of steps if training on less than, or more than, the noted three steps. The described supervised or unsupervised learning processes may include fusion learning, deep learning processes, or other known learning procedures. Furthermore, a multi-level learning process may be employed in which a predefined number of levels are used to detect the hand region, a second predefined number of levels are employed to detect the finger-pill-finger region, and a third predefined number of regions are employed to detect the pill. In such a manner, the images need only be passed through the system one time, each of the regions being defined as noted. While the process of hand reason, finger-pill-finger region and other predefined regions are described, any number of layers related to any patient self administration of medication or other medication are applicable to the present system. Therefore, while the section of pills in the hand of the user is shown, detection of use of an inhaler, injectable medication, reading a value off of a glucose meter or other medical device, or any other medication administration process may be addressed in accordance with various embodiments of the present invention.

Figure 2:
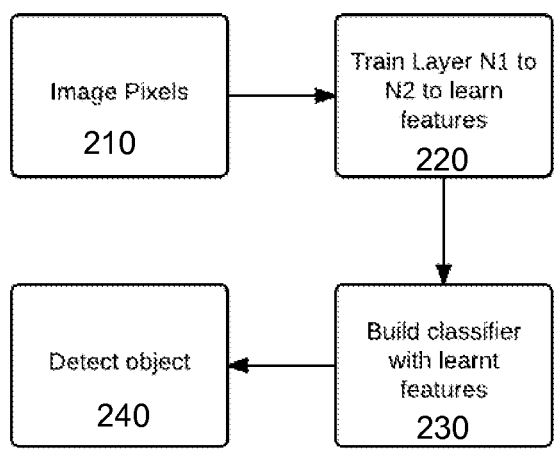
FIG. 2 is a flowchart diagram depicting a method for training a computer system using a learning process in accordance with an embodiment of the invention.

Referring next to FIG. 2, a process for training each of the first, second and third networks is described. As is shown in FIG. 2, pixels are imaged from the one or more acquired images at step 210. After acquisition, processing passes to step 220, wherein a plurality of training levels N1-N2 are employed to learn the features of target objects in the acquired images in accordance with known unsupervised or supervised learning techniques. While two layers are shown, any number of layers may preferably be employed, and indeed, each such interface between two levels may be applied any number of time, such as the number of times as described above with respect to FIG. 1. Processing then passes to step 230 where a classifier is then built employing one or more of features learned from step 220. Finally, an object may be detected at step 240 employing the classifier built at step 230.

Figure 3:
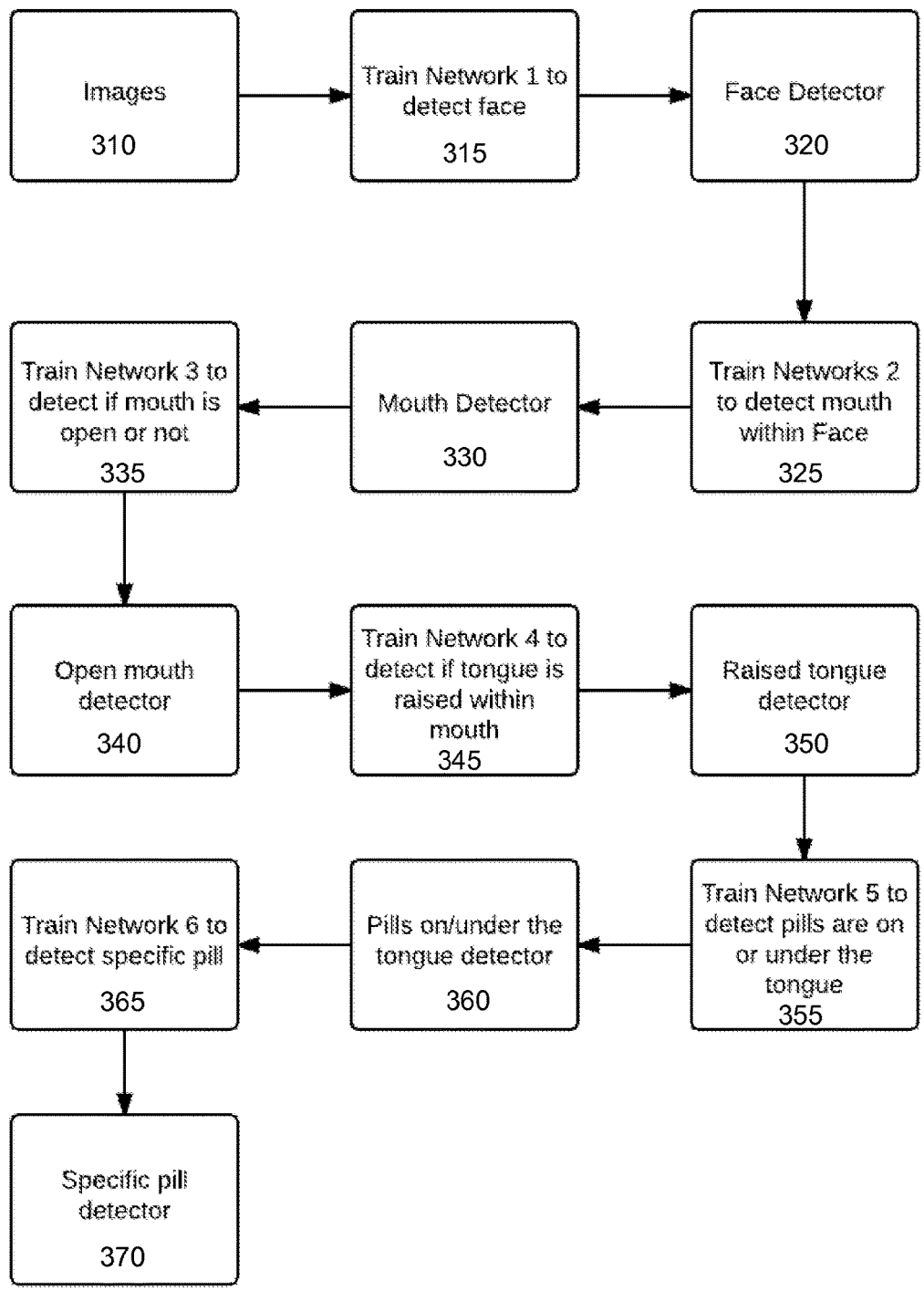
FIG. 3 is a flowchart diagram depicting a method for training a computer system in accordance with an embodiment of the invention.

Referring next to FIG. 3, a method for training a computer system for assisting in determining proper medication adherence is provided. While the embodiment depicted in FIG. 3 describes a medication adherence and administration process for the administration of oral medication, such as one or more pills or tablets, to injectable, inhalable, sublingual, or other medication administration processes. Each situation, a plurality of particular steps may be defined, each of such steps taking the place of one of the steps as will be described in accordance with FIG. 3. In keeping with various embodiments of FIG. 3, each network may therefore be used in training the system to recognize one of the predefined steps above. As is shown in FIG. 3, one or more images are acquired at step 310. Preferably, in accordance with one or more embodiments of the present invention, such images are of a user performing a sequence of steps to administer a medication, such as including the face of a user, detecting a medication pill in the mouth of the user, and other images so related. Such images may comprise individual still images, or may include one or more sets of sequential images, or one or more video sequences. Processing then preferably passes to step 315, where a first network is employed in accordance with one or more supervised or unsupervised learning processes, such as those known to one of ordinary skill in the art, in order to train the computer system to recognize the face of the user. After such training has taken place, processing preferably passes to step 320 where the training data is employed in a face detector element for detecting the face of a future user when administering medication.

Processing then passes to step 325 where a second network is employed in accordance with one or more supervised or unsupervised learning processes, such as those known to one of ordinary skill in the art, in order to train the computer system to detect a mouth of the user within the detected face region of the user from the acquired one or more images. Such second network preferably builds on, or employs the first network employed in step 320. Thus, preferably, learning performed from the first network, or the output therefrom, is used as the input to the second network. In such a manner, the search space for the second network is bounded as the results from the first network are employed. Thus, this second network is preferably trained to determine a mouth region from the determined face regions identified by the first network. After such training has taken place, processing preferably passes to step 330 where the training data is employed in a mouth detector element for detecting the mouth region of a future user when administering medication.

Processing then passes to step 335 where a third network is employed in accordance with one or more supervised or unsupervised learning processes, such as those known to one of ordinary skill in the art, in order to train the computer system to recognize whether the detected mouth of the user is open or not from the acquired one or more images. Such third network preferably builds on, or second the first network employed in step 320. Thus, preferably, learning performed from the second network, or the output therefrom, is used as the input to the third network. In such a manner, the search space for the second network is bounded as the results from the first network are employed. Thus, this second network is preferably trained to determine whether the mouth of the user is open or not from the determined mouth regions identified by the second network. After such training has taken place, processing preferably passes to step 340 where the training data is employed in an open mouth detector element for detecting whether the mouth of the user is open or closed when a future user is administering medication.

Processing then preferably passes to step 345, where a fourth network is employed in accordance with one or more supervised or unsupervised learning processes, such as those known to one of ordinary skill in the art, in order to train the computer system to recognize whether the tongue of a user is raised within the detected mouth of the user. Such fourth network preferably builds on, or employs the third network employed in step 335. Thus, preferably, learning performed from the third network, or the output therefrom, is used as the input to the fourth network. In such a manner, the search space for the fourth network is bounded as the results from the third network are employed. Thus, this fourth network is preferably trained to determine whether the tongue of a user is raised from the determined open mouth regions identified by the third network. After such training has taken place, processing preferably passes to step 350 where the training data is employed in a raised tongue detector element for detecting the face of a future user when administering medication.

Processing then passes to step 355 where a fifth network is employed in accordance with one or more supervised or unsupervised learning processes, such as those known to one of ordinary skill in the art, in order to train the computer system to detect whether on or more medication pills are located on or under the mouth of the user from the acquired one or more images. Such fifth network preferably builds on, or employs the third and/or fourth networks employed in steps 335 and/or 345. Thus, preferably, learning performed from the third and fourth network, or the output therefrom, is used as the input to the fifth network. In such a manner, the search space for the fifth network is bounded as the results from the third and/or fourth networks are employed. Thus, this fifth network is preferably trained to determine a pill in mouth or under tongue region from the determined mouth and lifted tongue regions identified by the third and/or forth networks. After such training has taken place, processing preferably passes to step 360 where the training data is employed in a pill on/under tongue detector element for detecting the whether a medication pill is located on/under the tongue of a future user when administering medication.

Processing then passes to step 365 where a sixth network is employed in accordance with one or more supervised or unsupervised learning processes, such as those known to one of ordinary skill in the art, in order to train the computer system to recognize the identity of a particular medication pill from the acquired one or more images. Such sixth network preferably builds on, or employs the fifth network employed in step 355. Thus, preferably, learning performed from the fifth network, or the output therefrom, is used as the input to the sixth network. In such a manner, the search space for the sixth network is bounded as the results from the fifth network are employed. Thus, this sixth network is preferably trained to properly identify a medication pill from the determined pill on or under tongue regions identified by the fifth network. After such training has taken place, processing preferably passes to step 370 where the training data is employed in a pill identity detector for recognizing the identity of a medication pill when a future user is administering medication.

While the method has been described in a particular order, it is possible that any order of training and deployment may be employed. Further, it is possible to use any sub-group of steps if training on less than, or more than, the noted set of steps. Furthermore, a multi-level learning process may be employed in which a predefined number of levels are used to detect each of the noted regions. In such a manner, the images need only be passed through the system one time, each of the regions being defined as noted. The described supervised or unsupervised learning processes may include fusion learning, deep learning processes, or other known learning procedures. While a medication pill is described, a medication tablet, capsule, film or the like may be employed in accordance with one or more alternative embodiments of the invention.

Figure 4:
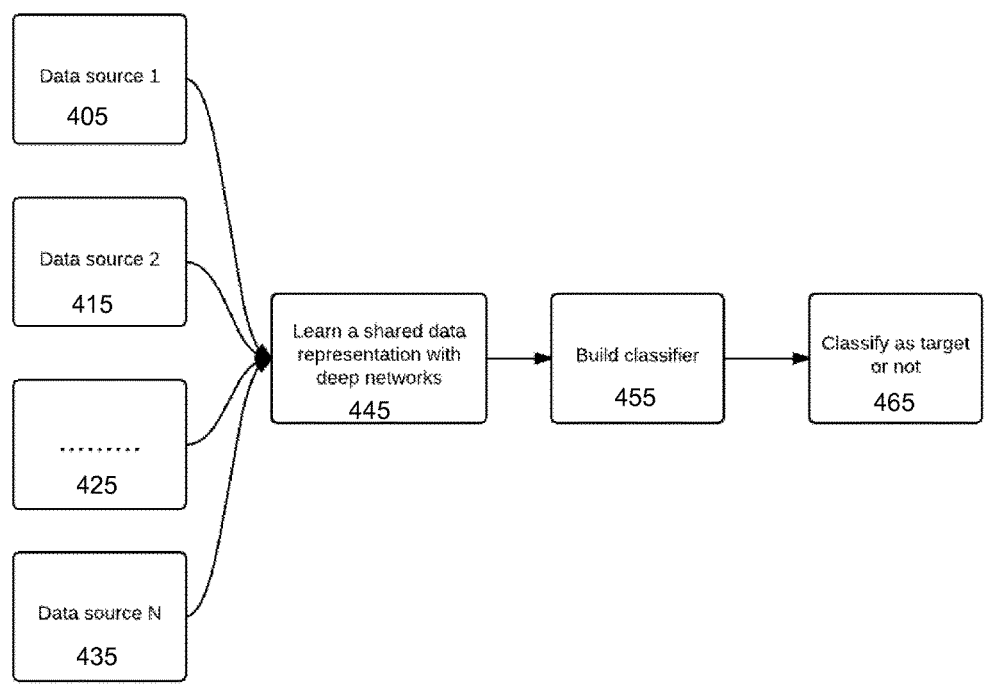
FIG. 4 is a flowchart diagram depicting a method for training a computer system using a data source combination using a learning process in accordance with an embodiment of the invention.

Referring next to FIG. 4, a method for training a computer system using a data source combination process employing an unsupervised or supervised learning process in accordance with an embodiment of the invention is shown. As is shown in FIG. 4, a plurality of data sources 1-N (see elements 405, 415, 425, 435) where one or more different types of data are acquired. Such data sources may include one or more of image data, video data, audio data, time on task data, adherence data, etc., or any other types of original or derivative data. Such data may further include one or more pieces of information entered by another user, such as a doctor, healthcare professional, or other individual. Such data may also include one or more pieces of information self-reported by the user, such as in response to one or more questions posed to the user at an appropriate time. Such data may further comprise one or more derivative forms of data accumulated in response to medication adherence monitoring data. For example, the input data my comprise one or more bits of information that describe one or more patients' characteristics. These features may be provided to the noted classifier (see step 445 below) to profile patients from the long term perspective and predict patients' behavior over a next short period of time. In addition, intervention data, such as when a health care provider intervenes with a patient, may be employed to predict which interventions are most likely to be successful. Thus, it is possible to also use the inventive framework to learn the relationship between the features of intervention data and the features of multiple sources data collected from patient. In such a manner, the below classifier 445 may be built to suggest a most effective intervention strategy to a particular patient.

In this particular embodiment of the invention, this data is preferably provided to an unsupervised or supervised learning process, preferably employing a deep neural networks. Such a process is preferably similar to one or more of the above-described learning processes, where the input data may be comprised from any of the above noted sources. In accordance with this preferred embodiment of the invention, the shared data representations are preferably related to determining whether one or more steps associated with proper administration have been properly performed.

Once processing at step 445 has been completed, processing passes to step 455, where a classifier is built to allow for the classification of future data. In accordance with various embodiments of the present invention, the future data is preferably related to the proper administration of medication. Finally, at step 465, upon use for monitoring medication administration, data is acquired from one or more of data sources 1-N, and then this data is classified as a targeted, desired action, preferably in accordance with proper medication administration. Also, additional human input and more data collected as time goes by may be employed to continuously or intermittently update the learning process to improve performance of the system over time.

Figure 5:
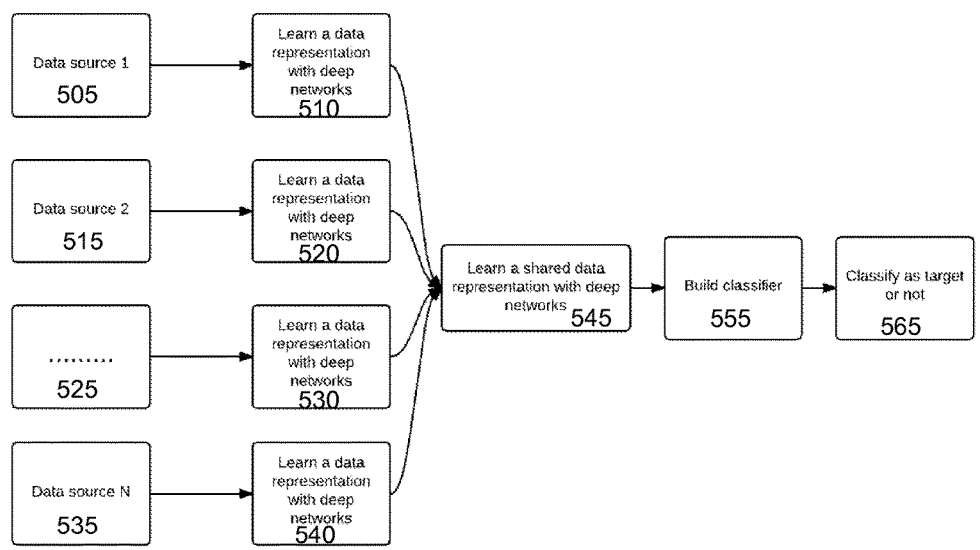

Referring next to FIG. 5, a method for training a computer system using a data source combination process employing an unsupervised or supervised learning process in accordance with an embodiment of the invention is shown. As is shown in FIG. 5, a plurality of data sources 1-N (see elements 505, 515, 525, 535) where one or more different types of data are acquired. Such data sources may include one or more of image data, video data, audio data, time on task data, adherence data, etc., or any other types of original or derivative data. In this particular embodiment of the invention, each individual data acquired from each individual data source is preferably provided to a corresponding unsupervised or supervised learning process (510, 520, 530, 540). Each such learning process is preferably similar to one or more of the above-described learning processes. In accordance with this preferred embodiment of the invention, the shared data representations are preferably related to determining whether one or more steps associated with proper administration have been properly performed.

After such individual learning processes are employed, the learned data is then preferably provided to an unsupervised or supervised learning process, preferably employing a deep neural network at step 545. Such a process is preferably similar to one or more of the above-described learning processes, where the input data may be comprised from any of the above noted sources. In accordance with this preferred embodiment of the invention, the shared data representations are preferably related to determining whether one or more steps associated with proper administration have been properly performed.

Once processing at step 545 has been completed, processing passes to step 555, where a classifier is built to allow for the classification of future data. In accordance with various embodiments of the present invention, the future data is preferably related to the proper administration of medication. Finally, at step 565, upon use for monitoring medication administration, data is acquired from one or more of data sources 1-N, and then this data is classified as a targeted, desired action, preferably in accordance with proper medication administration.

Figure 6:
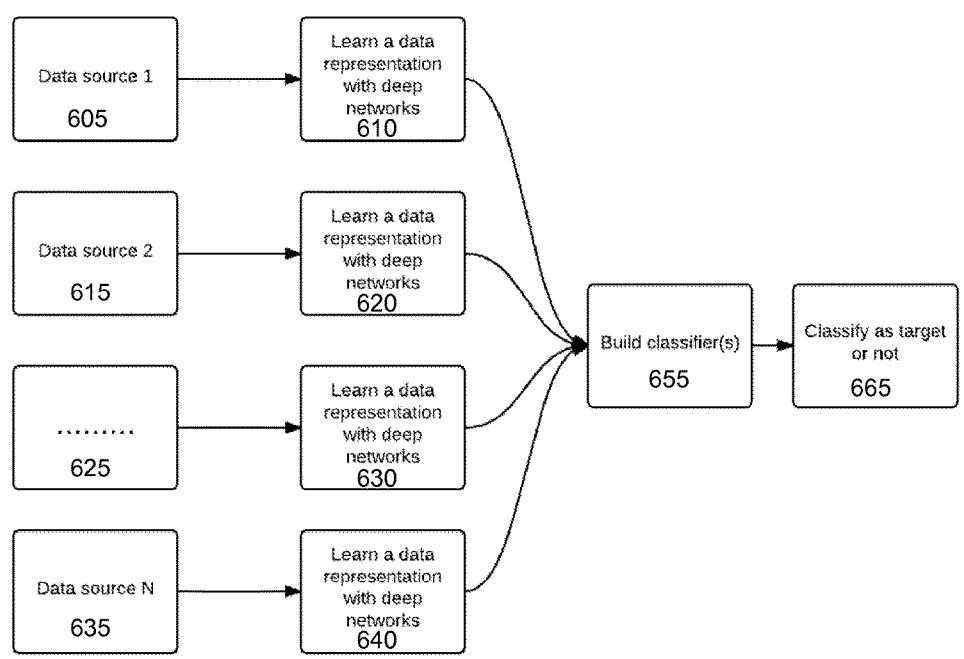
FIG. 6 is a flowchart diagram depicting a method for training a computer system using an additional data source combination using a plurality of learning processes.

Referring next to FIG. 6, a method for training a computer system using a data source combination process employing an unsupervised or supervised learning process in accordance with an embodiment of the invention is shown. As is shown in FIG. 6, a plurality of data sources 1-N (see elements 605, 615, 625, 635) where one or more different types of data are acquired. Such data sources may include one or more of image data, video data, audio data, time on task data, adherence data, etc., or any other types of original or derivative data. In this particular embodiment of the invention, each individual data acquired from each individual data source is preferably provided to a corresponding unsupervised or supervised learning process (610, 620, 630, 640). Each such learning process is preferably similar to one or more of the above-described learning processes. In accordance with this preferred embodiment of the invention, the shared data representations are preferably related to determining whether one or more steps associated with proper administration have been properly performed.

Once processing at steps 610, 620, 630, 640 have been completed, processing passes to step 655, where a classifier is built to allow for the classification of future data. In accordance with various embodiments of the present invention, the future data is preferably related to the proper administration of medication. Finally, at step 665, upon use for monitoring medication administration, data is acquired from one or more of data sources 1-N, and then this data is classified as a targeted, desired action, preferably in accordance with proper medication administration.

As the system is employed over time, additional input images may be employed to further train any of the one or more detectors as noted above. Thus, various facial features, etc. may shift over time, and the addition of these further images to a training set of images may be employed in order to further update the recognition properties of the system. In such a manner, it is contemplated that any of the particular recognition tasks may be kept up to date, and adjust to changing conditions, while maintaining a proper recognition. Thus, if the system is employed to recognize the face of a user to determine the identity thereof, as the person ages, or their face otherwise changes, these additional images may be employed in a training sequence as described above in order to further allow for flexibility and accuracy in the recognition task.

While various embodiments of the invention describe the use of video, image, and other data, the use of audio, derivative, or other data alone or in combination, is contemplated in accordance with the various embodiment of the invention, any other adherence data may be employed. For example when trying to determine proper medication administration by a user, historical adherence data or other information may be combined with other input data to aid in determining patient activity It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description and the following claims are intended to cover all of the generic and specific features of the invention herein described and all statements of the scope of the invention which, as a matter of language, might be said to fall there between.

What is claimed:

1. A method for training a medication administration monitoring apparatus, comprising the steps of:
    defining one or more predetermined medications;
    acquiring one or more images of a user administering medication;
    training a first deep neural network utilizing one or more learning processes to recognize a face portion of a user from the one or more images;
    training a second deep neural network utilizing one or more learning processes to recognize a mouth portion of the user from the one or more images based upon at least an output generated from the training of the first deep neural network;
    training a third deep neural network utilizing one or more learning processes to recognize an open mouth of the user from the one or more images based upon at least an output generated from the training of the second deep neural network;
    training a fourth deep neural network utilizing one or more learning processes to recognize a raised tongue of the user from the one or more images based upon at least upon an output generated from the training of the third deep neural network;
    training a fifth deep neural network utilizing one or more learning processes to recognize a medication pill on or under the tongue of the user from the one or more images based upon at least an output generated from the training of the fourth deep neural network; and
    training a sixth deep neural network utilizing one or more learning processes to recognize the identity of the medication pill from the one or more images based upon at least an output generated from the training of the fifth deep neural network.

2. The method of claim 1, wherein the training of each network is performed in accordance with a supervised learning process.

3. The method of claim 1, wherein the training of each network is performed in accordance with an unsupervised learning process.

4. The method of claim 1, wherein the training of a plurality of the networks are performed in sequence, employing the image processing system a single time.

5. The method of claim 1, wherein upon use of the trained networks to process images, utilizing one or more of these processed images to further train one or more of the networks.

6. The method of claim 1, further comprising the steps of:
    receiving audio data associated with the medication administration; and
    employing the received audio data to at least in part train one or more of the networks.

7. The method of claim 1, further comprising the steps of:
    receiving manually input data associated with the medication administration; and
    employing the manually input data associated with the medication administration.

8. The method of claim 7, wherein the manually input data is received from the user.

9. The method of claim 7, wherein the additional input data is system generated data.

10. The method of claim 1, further comprising the step of confirming that the one or more predetermined medications cover a desired spectrum of possible medications.

* * * * *